(12) United States Patent
     Cook

(10) Patent No.: US 10,556,078 B2
(45) Date of Patent: Feb. 11, 2020

(54) CAMERA TUBE WITH GUIDE SURFACE FOR INTUBATION STYLET AND METHOD OF USE

(71) Applicant: Cookgas, LLC, St. Louis, MO (US)

(72) Inventor: Daniel J. Cook, St. Louis, MO (US)

(73) Assignee: COOKGAS, LLC, St. Louis, MO (US)

( * ) Notice: Subject to any disclaimer, the term of this patent is extended or adjusted under 35 U.S.C. 154(b) by 490 days.

(21) Appl. No.: 15/480,667

(22) Filed: Apr. 6, 2017

(65) Prior Publication Data

US 2017/0209660 A1    Jul. 27, 2017

Related U.S. Application Data

(62) Division of application No. 14/522,212, filed on Oct. 23, 2014, now Pat. No. 9,833,587.

(51) Int. Cl.
    | | |
    |---|---|
    | *A61B 1/00* | (2006.01) |
    | *A61M 16/04* | (2006.01) |
    | *A61B 1/05* | (2006.01) |
    | *A61B 1/267* | (2006.01) |
    | *A61B 1/005* | (2006.01) |

(52) U.S. Cl.
    CPC ......... *A61M 16/0488* (2013.01); *A61B 1/005* (2013.01); *A61B 1/00073* (2013.01); *A61B 1/051* (2013.01); *A61B 1/2673* (2013.01); *A61M 16/0409* (2014.02); *A61M 16/0434* (2013.01); *A61M 16/0447* (2014.02); *A61M 2205/3306* (2013.01)

(58) Field of Classification Search
     None
     See application file for complete search history.

(56) References Cited

U.S. PATENT DOCUMENTS

| | | | |
|---|---|---|---|
| 4,437,458 A | | 3/1984 | Upsher |
| 5,329,940 A | | 7/1994 | Adair |
| 5,551,946 A | | 9/1996 | Bullard |
| 5,682,880 A | * | 11/1997 | Brain ................ A61M 16/0488 128/200.26 |

(Continued)

FOREIGN PATENT DOCUMENTS

| | | |
|---|---|---|
| CN | 101596336 A | 12/2009 |
| DE | 102007049191 A1 | 4/2009 |

(Continued)

*Primary Examiner* — Timothy J Neal
(74) *Attorney, Agent, or Firm* — Thompson Coburn LLP

(57) ABSTRACT

A method involves using a camera tube in connection with a laryngeal mask. The camera tube cooperates with an intubation stylet. The camera tube is an elongate member having a length extending between opposite distal and proximal ends. The distal end of the camera tube has a camera. The camera tube has an exterior surface and an intubation stylet guide support surface extending radially outward from the exterior surface along a portion of the length adjacent to the distal end. The intubation stylet guide support surface is configured to cooperate with an intubation stylet. The user may manipulate the proximal end of the camera tube to change the orientation of the intubation stylet with in the laryngeal mask while using the camera to visualize the patient's laryngeal opening. Once the intubation stylet is aligned with the patient's laryngeal opening, the intubation stylet may be advanced therethrough.

12 Claims, 12 Drawing Sheets

(56) References Cited

U.S. PATENT DOCUMENTS

| | | |
|---|---|---|
| 6,146,402 A | 11/2000 | Munoz |
| 6,322,498 B1 | 11/2001 | Gravenstein et al. |
| 6,354,993 B1 | 3/2002 | Kaplan et al. |
| 6,929,600 B2 | 8/2005 | Hill |
| 7,946,981 B1 | 5/2011 | Cubb |
| 2002/0068851 A1 | 6/2002 | Gravenstein et al. |
| 2007/0074720 A1 | 4/2007 | Schwartz et al. |
| 2007/0106122 A1 | 5/2007 | Yokota et al. |
| 2008/0236575 A1 | 10/2008 | Chuda |
| 2008/0236592 A1* | 10/2008 | Chen .................. A61M 16/04 128/207.15 |
| 2009/0227984 A1 | 9/2009 | Kizer |
| 2009/0318757 A1 | 12/2009 | Singh |
| 2010/0256451 A1 | 10/2010 | McGrath et al. |
| 2010/0261967 A1 | 10/2010 | Pacey et al. |
| 2010/0298643 A1 | 11/2010 | Eisele |
| 2010/0298644 A1 | 11/2010 | Kleene |
| 2010/0312059 A1 | 12/2010 | Mcgrath |
| 2011/0077466 A1 | 3/2011 | Rosenthal |
| 2011/0130627 A1* | 6/2011 | McGrail ............ A61B 1/00016 600/109 |
| 2011/0178372 A1 | 7/2011 | Pacey et al. |
| 2011/0270038 A1 | 11/2011 | Jiang et al. |
| 2012/0059223 A1 | 3/2012 | McGrath et al. |
| 2012/0095294 A1 | 4/2012 | Mcgrath et al. |
| 2013/0245372 A1 | 9/2013 | Lo |
| 2013/0310650 A1 | 11/2013 | Hales et al. |
| 2013/0319406 A1 | 12/2013 | Borrye |
| 2013/0345518 A1 | 12/2013 | Law et al. |
| 2014/0107422 A1 | 4/2014 | Huels et al. |
| 2014/0160261 A1 | 6/2014 | Miller et al. |
| 2015/0173598 A1 | 6/2015 | Alexander |

FOREIGN PATENT DOCUMENTS

| | | |
|---|---|---|
| JP | 2002000732 A | 1/2002 |
| TW | 201422266 A | 6/2014 |
| WO | 2010/150291 A1 | 12/2010 |

* cited by examiner

CAMERA TUBE WITH GUIDE SURFACE FOR INTUBATION STYLET AND METHOD OF USE

CROSS-REFERENCE TO RELATED APPLICATIONS

This application is a divisional application of application Ser. No. 14/522,212, filed on Oct. 23, 2014, and which is currently pending, the disclosure of which is incorporated by reference herein.

BACKGROUND AND SUMMARY

This disclosure relates to systems and methods of endo-tracheal intubation, including laryngeal masks, intubation stylets, and scopes, such as laryngoscopes and broncho-scopes, and their respective methods of use.

DETAILED DESCRIPTION

Figure 1:
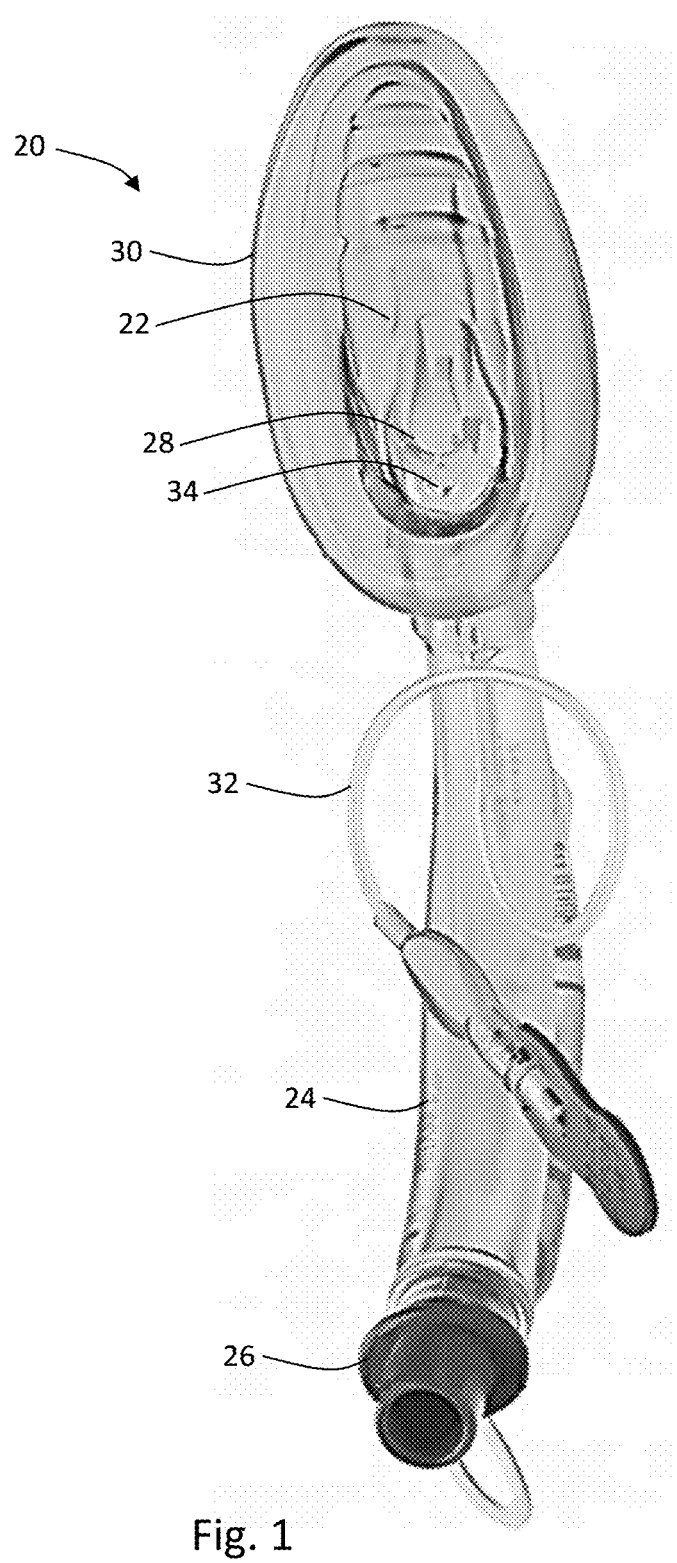
FIG. 1 shows an exemplary laryngeal mask.

The camera tube described herein may be used in connection with a laryngeal mask in order to facilitate use of an intubation stylet for endo-tracheal intubation. The laryngeal mask may be placed within a patient's oropharynx region over the laryngeal opening, and secured in place by means of air inflation. The laryngeal mask may be of the type described in U.S. Pat. Nos. 5,937,860; 6,422,239; 6,892,731; 7,331,347; 7,934,502; and 8,622,060. The aforementioned list of disclosures is incorporated by reference herein. Although a laryngeal mask of the type described in U.S. Pat. No. 5,937,860 is shown in the drawings, other laryngeal mask types may also be used in connection with the camera tube and intubation stylet described below.

Figure 2:
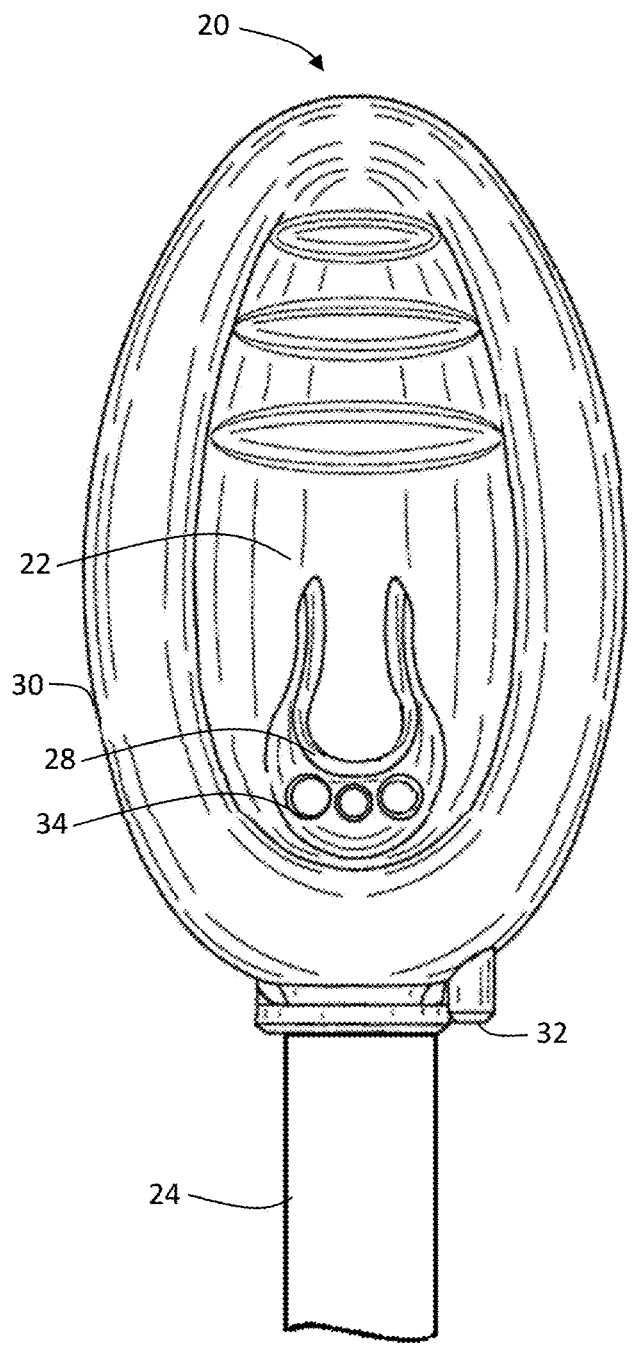
FIG. 2 shows another view of the laryngeal mask of FIG. 1.

FIGS. 1 and 2 provide detail of an exemplary laryngeal mask 20. The laryngeal mask 20 has a positioning shield 22 formed as a convex body that defines a cavity. A respiratory tube 24 extends from the positioning shield with a proximal end 26 having a connector configured connect to external ventilation and/or respiratory equipment (not shown) and a distal end 28 extending to the cavity of the positioning shield. The respiratory tube 24 and positioning shield 22 may be made from a relatively soft flexible material such as, but not limited to, silicone-rubber polymer or plastics. The positioning shield 22 may have a flexible sealing ring 30 around its periphery that surrounds the cavity defined by the positioning shield. The sealing ring 30 is shaped to conform to the patient's oropharynx region without distortion or causing displacement of surrounding tissue. The sealing ring 30 may comprise a number of different structures and may be ellipsoidal, toroidal, or a similar circular shape. The sealing ring 30 may have an inner volume, which may be generally sealed, or more open depending upon the application and the type of laryngeal mask. The sealing ring 30 may be inflated through a tube 32 placed in communication with an external inflation source (not shown). The sealing ring 30 may also be inflated by differential pressure supplied to the airway during pressurization of the cavity of the positioning shield in connection with the patient's ventilation. The distal end 28 of the respiratory tube 24 may be formed at an angle as it projects into the cavity so as to define an elongated elliptical shape. The shape may also be keyhole, oval, or circular depending upon the application. The distal end 28 of the respiratory tube 24 may project into the cavity and form an elevation ramp to facilitate intubation and deviation of the epiglottis. The distal end 28 of the respiratory tube 24 may also include alternative ventilation lumens 34 that communicate with the respiratory tube and assist in providing an airway in the event the distal end 28 of the respiratory tube becomes blocked. The airway may also have a gastric drainage tube (not shown) placed lateral to respiratory tube to allow any regurgitated gastric contents to bypass the glottis.

Figure 3:
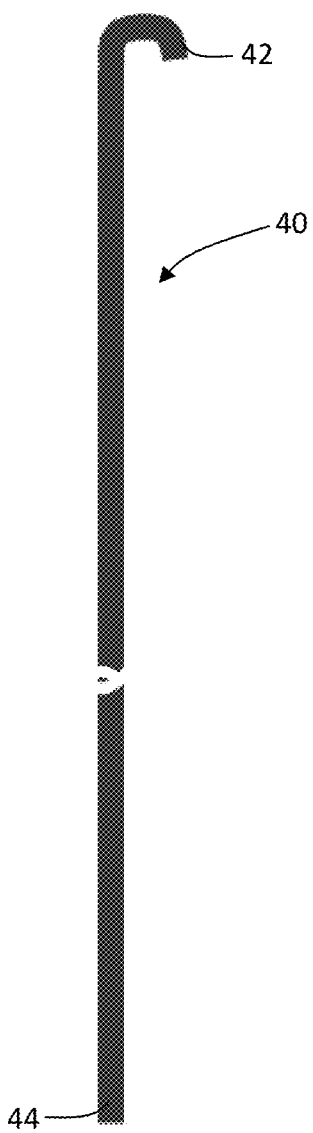
FIG. 3 shows an exemplary intubation stylet.
Figure 4:
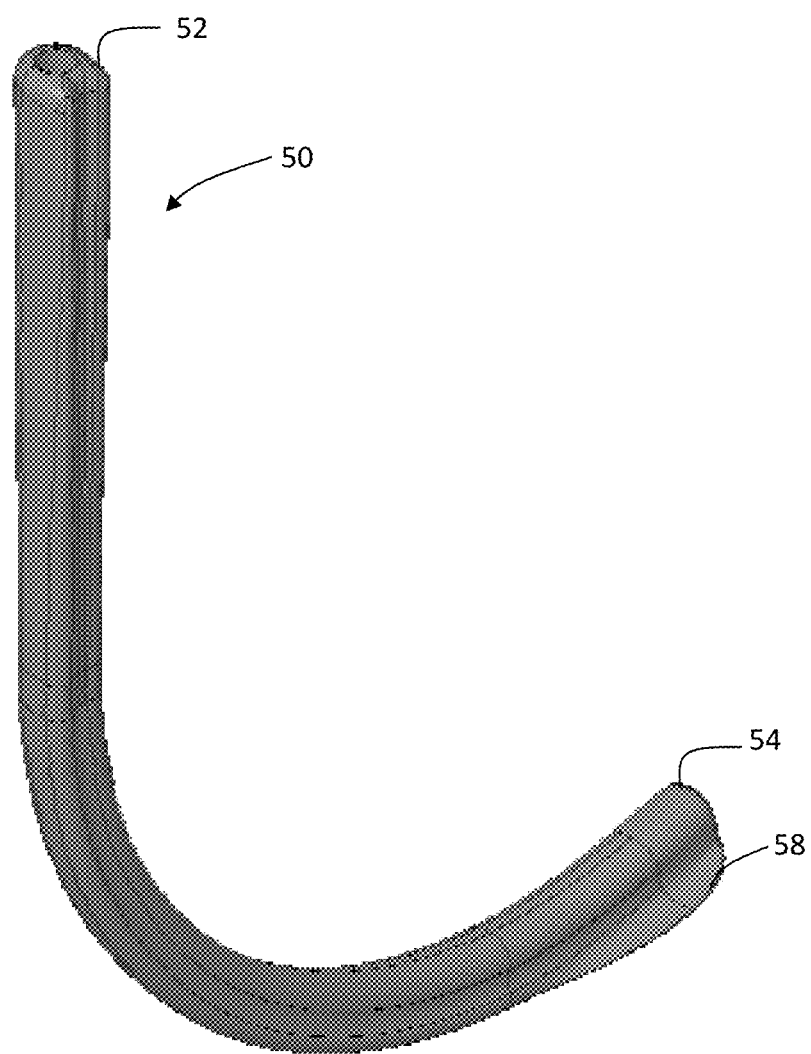
FIG. 4 shows a back perspective view of an exemplary camera tube.
Figure 5:
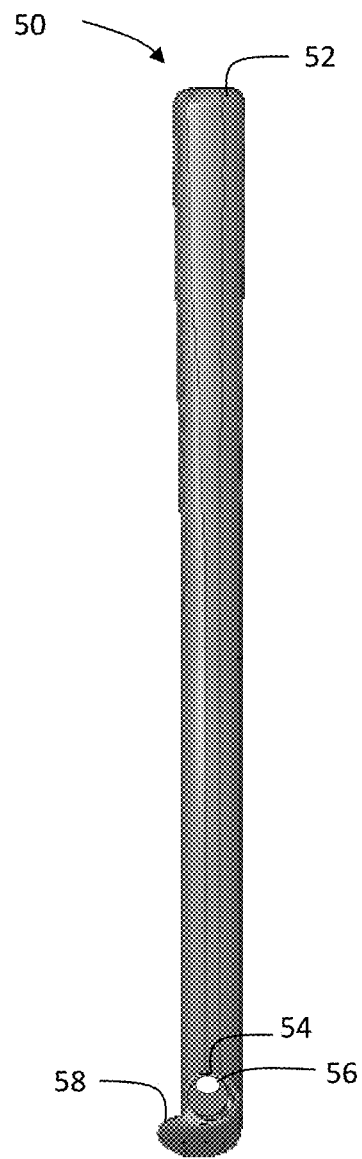
FIG. 5 shows a front view of the camera tube of FIG. 4.
Figure 6:
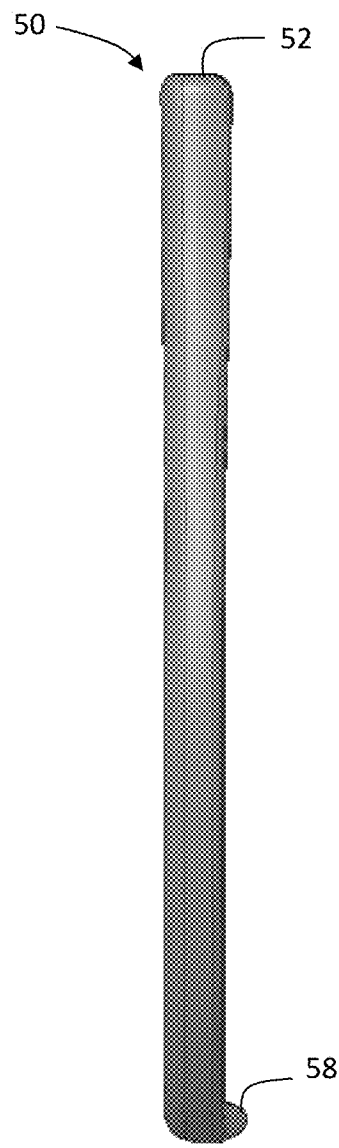
FIG. 6 shows a back view of the camera tube of FIG. 5.
Figures 7, 8:
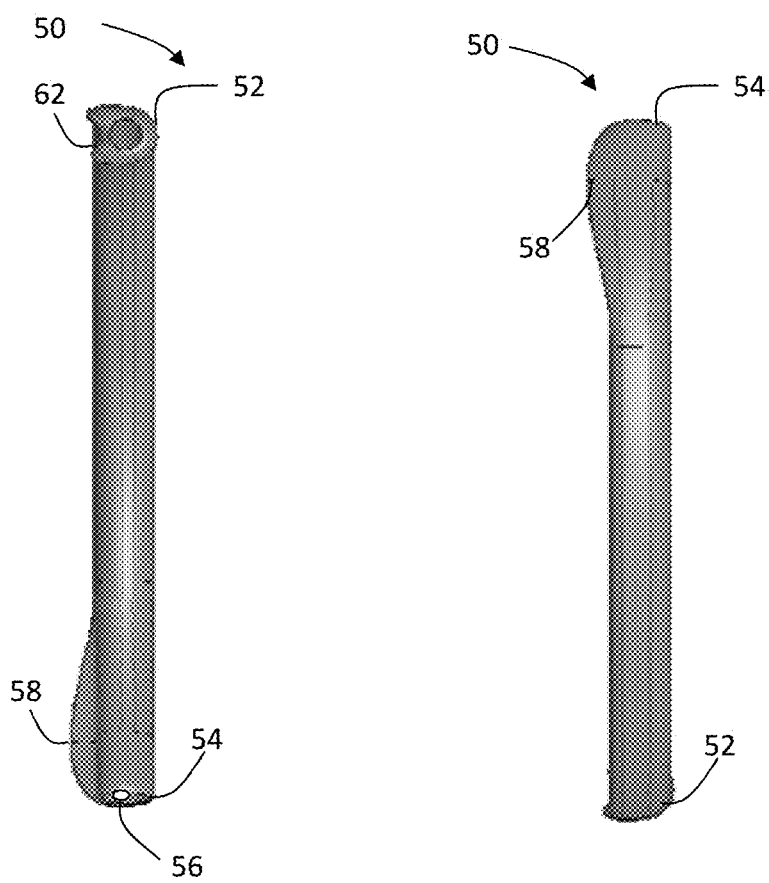
FIG. 7 shows a top view of the camera tube of FIG. 5.
FIG. 8 shows a bottom view of the camera tube of FIG. 5.
Figure 9:
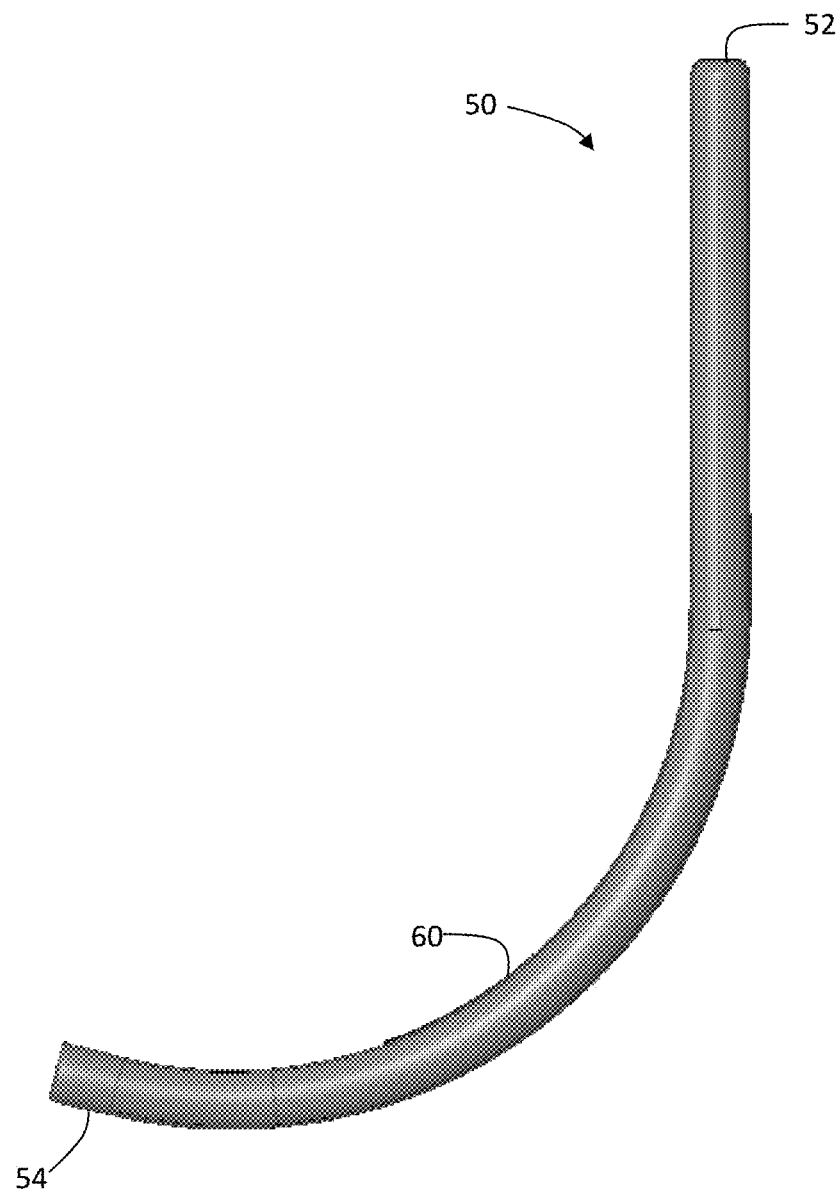
FIG. 9 shows a right side view of the camera tube of FIG. 5.
Figure 10:
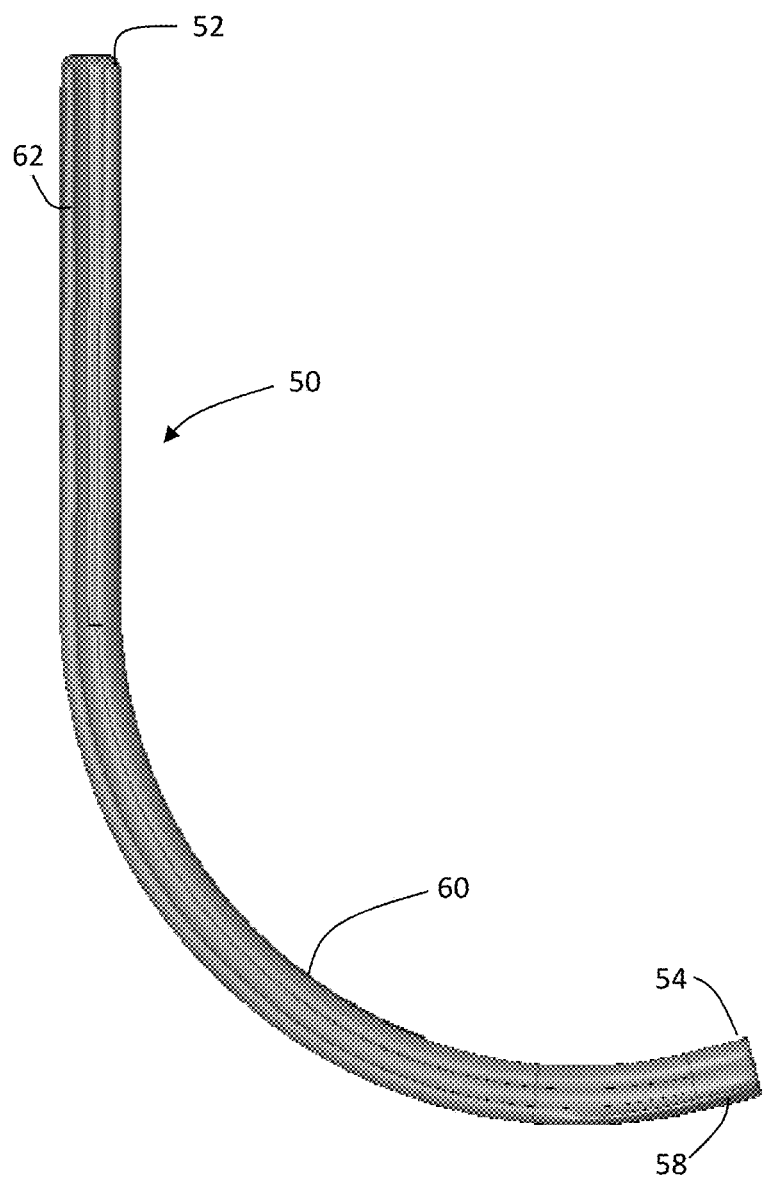
FIG. 10 shows a left side view of the camera tube of FIG. 5.
Figure 11:
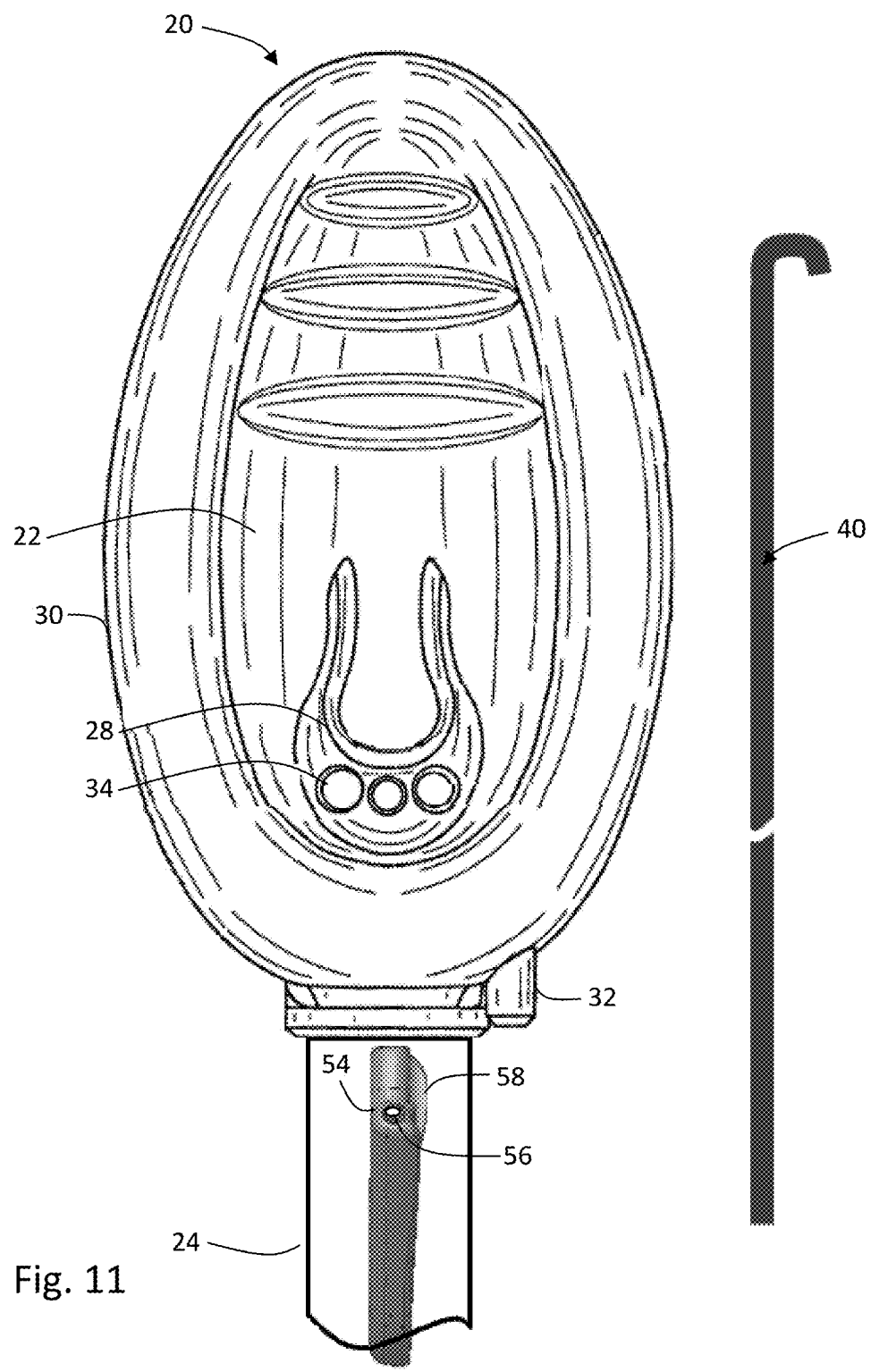
FIG. 11 shows the camera tube of FIGS. 4-10 being inserted into a respiratory tube of the laryngeal mask of FIG. 2 and the intubation stylet of FIG. 3 staged for use.
Figure 12:
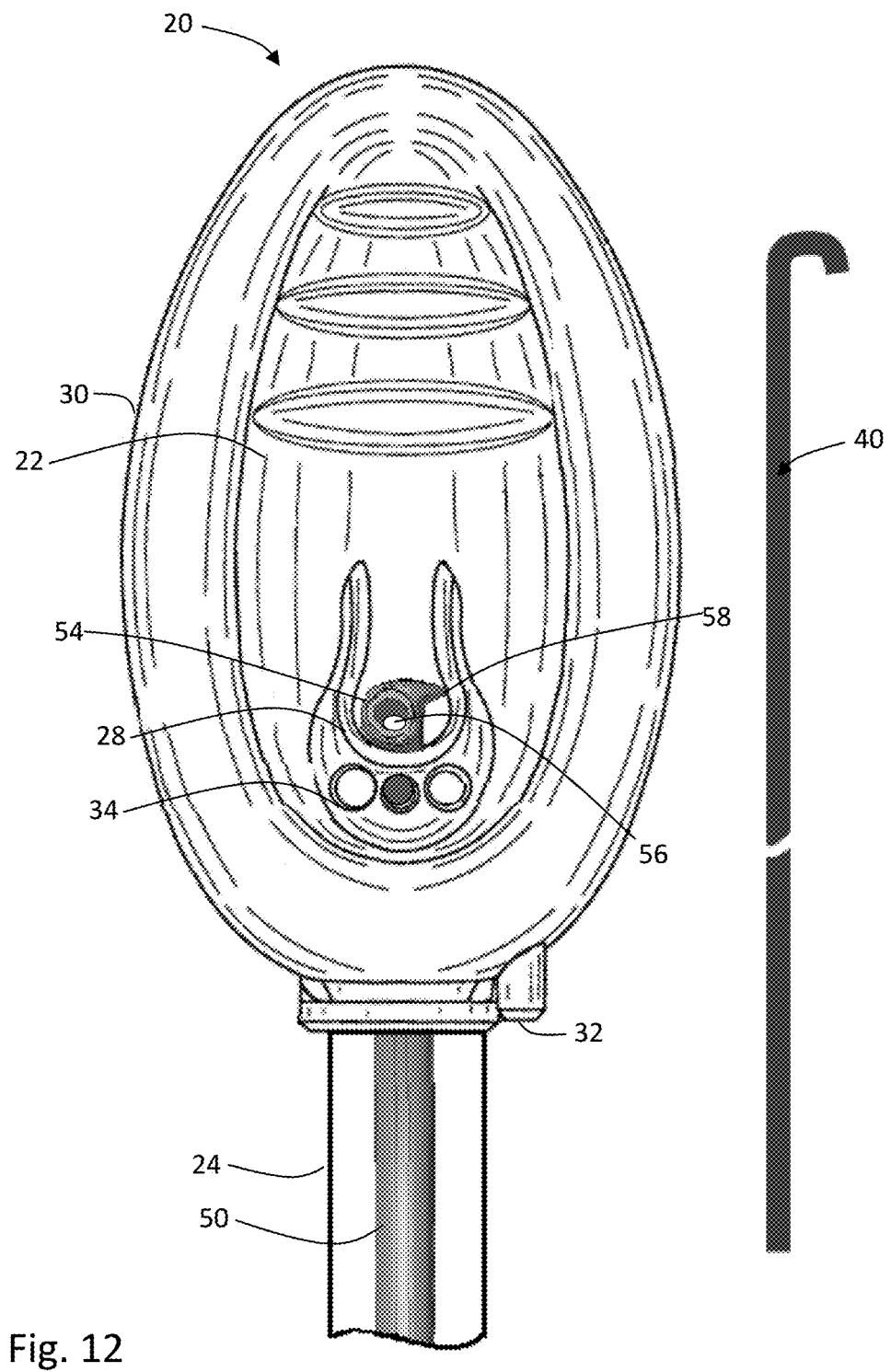
FIG. 12 shows the camera tube inserted through the respiratory tube and into the cavity of the laryngeal mask, and the intubation stylet of staged for use.
Figure 13:
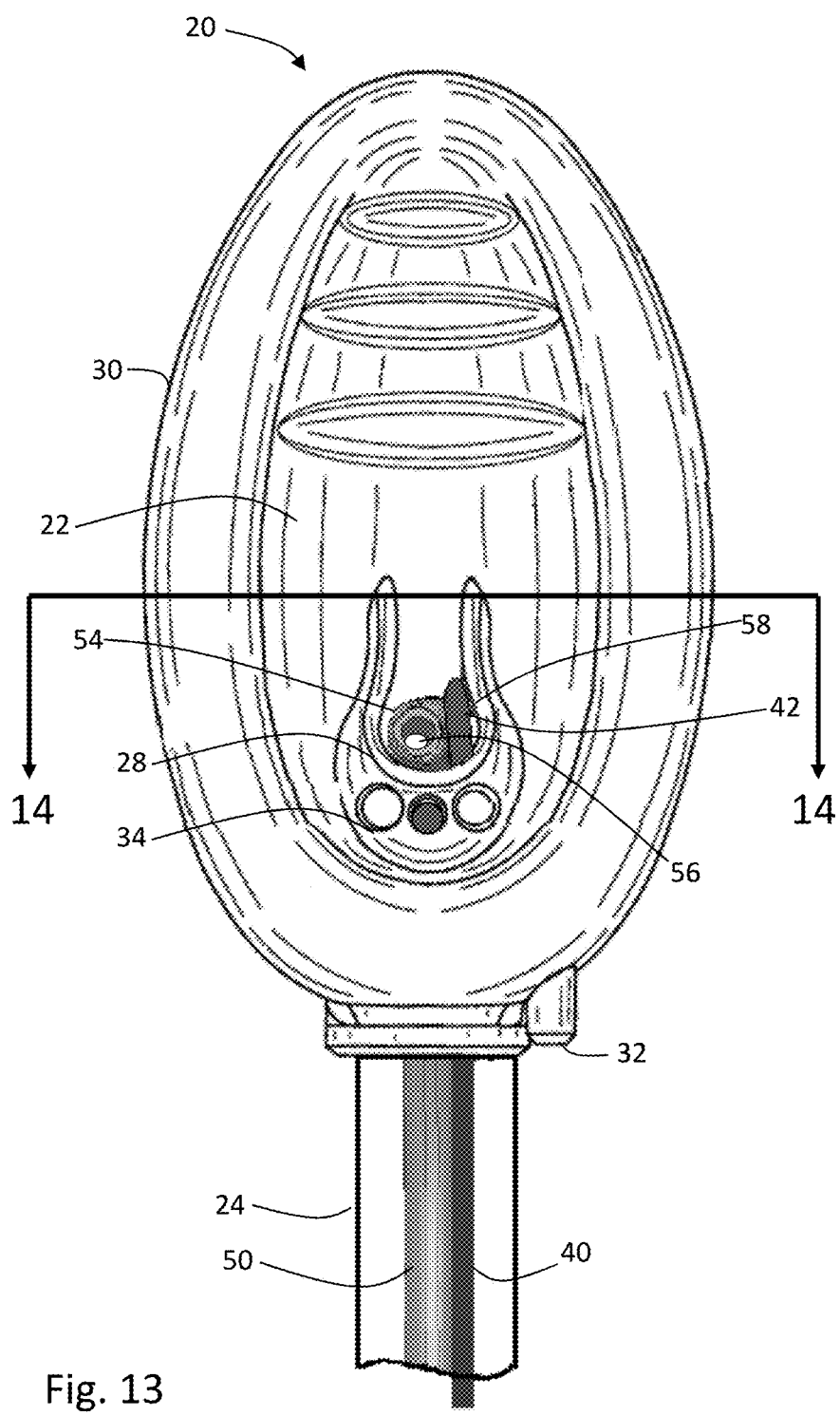
FIG. 13 shows the intubation stylet being inserted through the respiratory tube of the laryngeal mask such that the distal end of the intubation stylet is positioned adjacent to the distal end of the camera tube.
Figure 14:
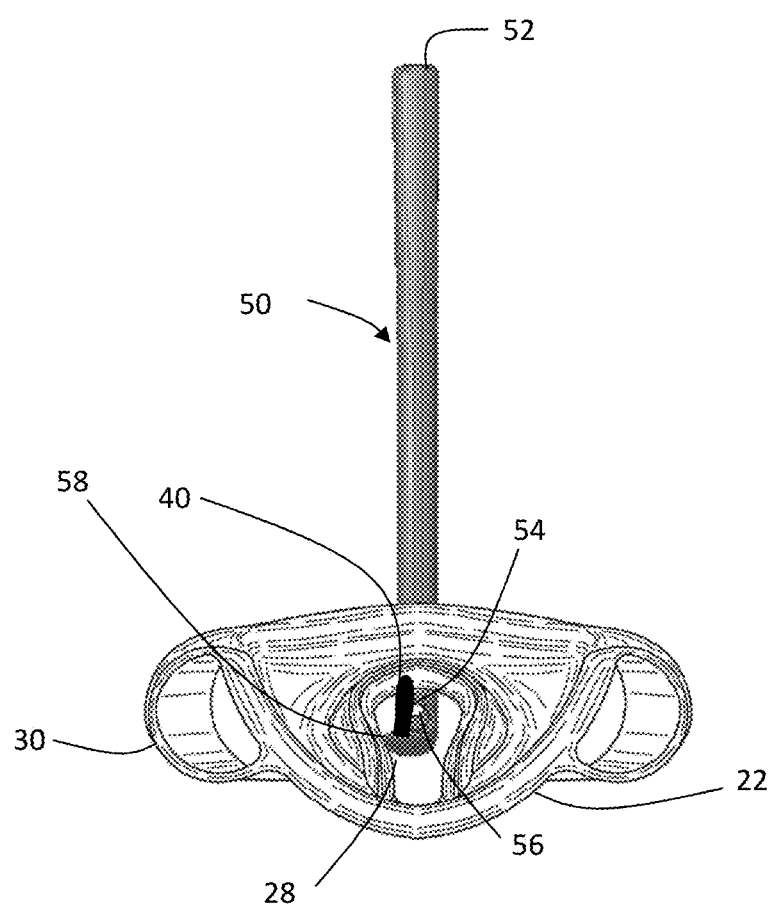
FIG. 14 is a cross-sectional view of the mask taken along section lines 14-14 of FIG. 13 to show the position of the camera tube and the intubation within the respiratory tube distal end.
Figure 15:
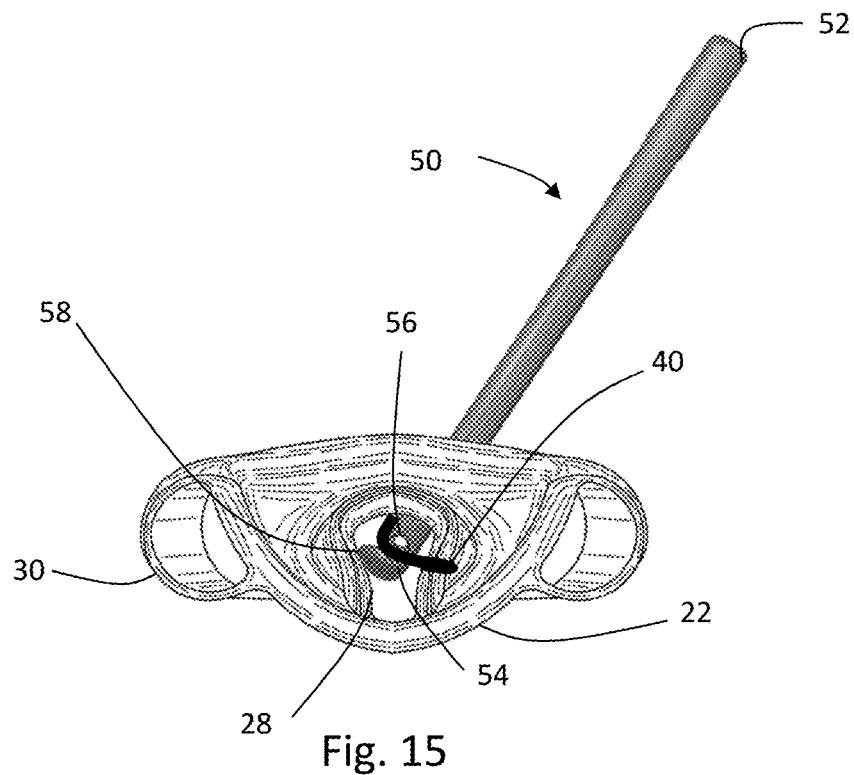
FIGS. 15 and 16 are views similar to FIG. 14 showing the camera tube being rotated to orient the distal end of the intubation stylet within the cavity of the laryngeal mask.
Figure 16:
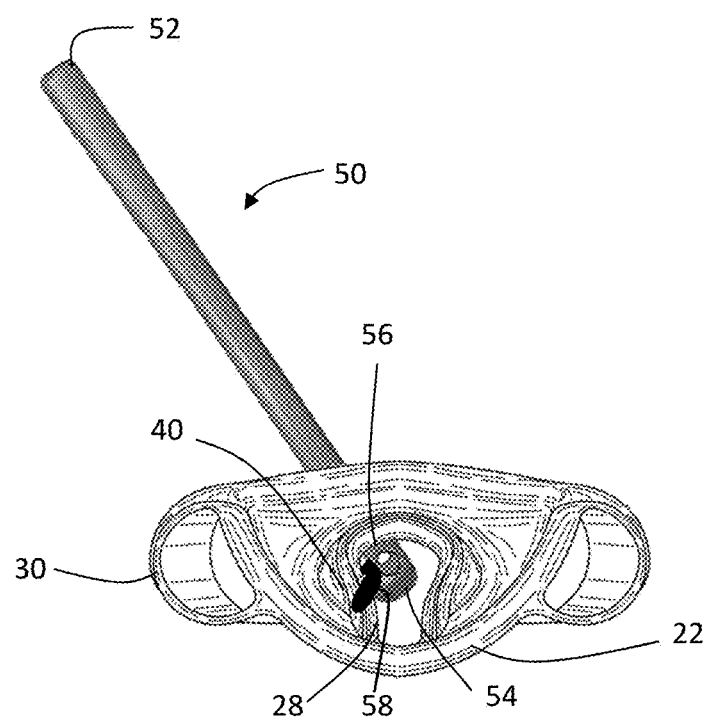

FIG. 3 shows an exemplary intubation stylet 40. The stylet has a distal end 42 directable to the patient's laryngeal opening and a proximal end 44 that may be manipulated by the user to advance the distal end as necessary.

FIGS. 4-10 show an exemplary camera tube 50. The camera tube 50 may be insertable through the respiratory tube 24 into the cavity of the positioning shield 22 to allow visualization of the patient's oropharynx region. The camera tube 50 generally comprises an elongate member with proximal and distal ends 52,54. The distal end 54 may have a recess configured to receive a camera element 56. The camera element 56 may be situated in the distal end 54 of the camera tube 50 such that it is offset from a center of the tube. Wire connections and other sensors associated with operation of the camera element 56 may be disposed within a hollow interior of the camera tube that extends through the length of the camera tube from the distal end 54 adjacent to the camera element to the proximal end 52. The proximal end 52 may be provided with connectors (not shown) configured to connect to image processing equipment (not shown). The distal end 54 of the camera tube 50 may be formed with an intubation stylet guide support surface 58. The intubation stylet guide support surface 58 may extend radially outward from an exterior surface of the camera tube and may be curved or otherwise shaped to cooperate with the intubation stylet 40. The intubation stylet guide support surface 58 may extend from a distal end 54 of the camera tube along a portion of the length of the camera tube. The intubation stylet guide support surface 58 may be contiguous or interrupted. The intubation stylet guide support surface 58 may have a peripheral edge which is shaped to conform to the distal end 28 of the respiratory tube 24 at its entry into the cavity. The intubation stylet guide support surface may contact inner wall portions of the respiratory tube 24 adjacent the distal end 28 of the respiratory tube so as to form an aperture between the intubation stylet guide support surface 58 and the respiratory tube distal end through which the intubation stylet 40 may pass as it is introduced through the respiratory tube into the cavity. The intubation stylet guide support surface 58 may be offset from a center of the camera tube distal end 54 to account for the diameter of the intubation stylet 40 such that the center of the intubation stylet corresponds to the center of the distal end of the camera tube, only laterally offset by the radial dimensions of the camera tube and the stylet. With the camera element 56 offset from the center of the camera tube distal end, the user may have more of an unobstructed view of the intubation stylet and the patient's laryngeal opening.

The camera tube 50 may be adjustable allowing the user flexibility in adapting the camera tube to fit in the respiratory tube and for use with a particular patient. For instance, the camera tube 50 may be bendable along the camera tube length to produce a bend 60 of the type shown in FIGS. 4-10. The radius or curvature of the bend 60 may be such that when the camera tube 50 is introduced into the respiratory tube 24 of the laryngeal mask, the camera tube allows visualization of the intubation stylet 40 and the laryngeal opening of the patient. The camera tube 50 may be bendable anywhere along its length to allow customization of the camera tube for a particular patient. The camera tube 50 may also be pre-formed with a bend for a specific size laryngeal mask and specific size patient. By providing a bend 60 in the camera tube 50, the proximal end of the camera tube 52 may be manipulated within the airway as explained below to allow visualization of the laryngeal opening of the patient and the distal end 42 of the intubation stylet 40.

To facilitate use of the intubation stylet 40 with the camera tube 50, the camera tube may be provided with a groove 62 on its exterior surface that is configured to at least partially receive the intubation stylet. The groove 62 may extend from the proximal end 52 of the camera tube to the distal end 54 of the camera tube. The groove 62 may cooperate with the intubation stylet guide support surface 58 such that the distal end 42 of the intubation stylet 40 may be advanced in a seamless transition from the groove onto the intubation stylet guide support surface.

FIGS. 11-16 illustrate a sequence in introducing the intubation stylet to the patient's laryngeal opening. In operation, the laryngeal mask 20 may be placed in position adjacent the patient's oropharynx region. The camera tube 50 may be advanced through the respiratory tube 24 to the distal end 28 of the respiratory tube adjacent to the cavity of the positioning shield 22 (see, e.g., FIG. 11). The camera tube 50 may be bent as necessary in order to allow it to be advanced through the respiratory tube 24. The camera tube 50 may be inserted in the respiratory tube 24 of the laryngeal mask and manipulated such that the intubation stylet guide support surface 58 is positioned to abut the distal end 28 of the respiratory tube and the distal end 54 of the camera tube is just at the entrance to the cavity facing the patient's laryngeal opening (see, e.g., FIG. 12). The intubation stylet 40 may be introduced into the respiratory tube 24 and directed through the distal end 28 of the respiratory tube onto the intubation stylet guide support surface 58 (see, e.g., FIGS. 13-14). The intubation stylet 40 may be directed along the groove 62 of the camera tube 50 to the intubation stylet guide support surface 58. Utilizing the camera to visualize the intubation stylet distal end 42, the camera tube 50 may be manipulated in the airway to orient the intubation stylet distal end as desired and visualize its advancement into the cavity (see, e.g., FIGS. 15-16). Manipulation of the proximal end 52 of the camera tube 50 results in rotation of the distal end 54 of the camera tube and rotation of the intubation stylet guide support surface 58. This results in rotation of the distal end of the intubation stylet. The proximal end 52 of the camera tube may be manipulated as necessary to align the camera view and to align the distal end 42 of the intubation stylet at the laryngeal opening of the patient. The intubation stylet 40 may then be advanced through the laryngeal opening of the patient in preparation for introduction of an endo-tracheal tube or other instrumentation. Using the camera element 56 and manipulating the camera tube 50, the correct orientation of the intubation stylet 40 may be attained. Once the intubation stylet is in place through the laryngeal opening of the patient, the camera tube may be removed to facilitate installation of the endo-tracheal tube or other instrumentation through the respiratory tube. The endo-tracheal tube may be advanced over the stylet through the laryngeal opening. With the endo-tracheal tube in place, the mask may be removed. By providing the camera element 56 offset to a center of the distal end 54 of the camera tube 50, the line of sight provided by the camera element is less likely to be obstructed by the intubation stylet 40. Providing a bend 60 in the camera tube 50 enables the camera tube to in effect act as a joystick which facilitates the user in manipulating the proximal end 54 of the camera tube to provide the desired images of the laryngeal opening in order to advance the intubation stylet therethrough.

The camera tube 50 may be sold or distributed as part of a laryngeal mask kit. The intubation stylet 40 may be included with the kit. In the alternative, the camera tube 50 may be sold as a separate unit to be added or used in connection with a particular laryngeal mask and/or intubation stylet. In connection with the sale or distribution of the camera tube, a user (e.g., a purchaser of the camera tube) is instructed that the purpose of the camera tube is to use the camera tube in connection with a laryngeal mask and/or intubation stylet for the purpose of endo-tracheal intubation procedures. The user is induced to use the camera tube in connection with a laryngeal mask and/or intubation stylet. In connection therewith, the user is instructed to insert the camera tube in a laryngeal mask and insert an intubation stylet in the laryngeal mask such that the intubation stylet abuts the camera tube and is supported by the intubation stylet guide support surface and the distal end of the laryngeal mask. In connection therewith, the user is also instructed to manipulate the camera tube to change an orientation of the intubation stylet within the laryngeal mask.

As various modifications could be made in the constructions and methods herein described and illustrated without departing from the scope of the invention, it is intended that all matter contained in the foregoing description are shown in the accompanying drawings shall be interpreted as illustrative and not as limiting. The breadth and scope of the present invention should not be limited by any of the above-described exemplary embodiments but should be defined only in accordance with the following claims appended hereto and their equivalents.

What is claimed is:

1. A method comprising:
providing a camera tube wherein the camera tube comprises an elongate member having a length extending between opposite distal and proximal ends of the elongate member, the camera tube having a first imaginary line extending from a center of the proximal end and a second imaginary line extending from a center of the distal end, the distal end having a camera, the camera tube having an exterior surface and an intubation stylet guide support extending radially outward from the exterior surface along a portion of the length adjacent to the distal end;
directing a user to:
insert the camera tube in a laryngeal mask;
insert an intubation stylet in the laryngeal mask so that the intubation stylet abuts the camera tube and is supported by the intubation stylet guide support; and
manipulate the camera tube to change an orientation of the intubation stylet within the laryngeal mask.

2. The method of claim 1 further comprising directing the user to place the intubation stylet in a groove of the camera tube formed in the camera tube exterior surface.

3. The method of claim 2 wherein the step of directing the user to place the intubation stylet in the groove includes directing the user to advance the intubation stylet from the camera tube groove onto the intubation stylet guide support.

4. The method of claim 1 further comprising directing the user to bend the camera tube along its length to adjust an angle between the first and second imaginary lines.

5. A method comprising:
accessing a camera tube wherein the camera tube comprises an elongate member having a length extending between opposite distal and proximal ends of the elongate member, the camera tube having a first imaginary line extending from a center of the proximal end and a second imaginary line extending from a center of the distal end, the distal end having a camera, the camera tube having an exterior surface and an intubation stylet guide support extending radially outward from the exterior surface along a portion of the length adjacent to the distal end;
inserting the camera tube in a laryngeal mask;
inserting an intubation stylet in the laryngeal mask so that the intubation stylet abuts the camera tube and is supported by the intubation stylet guide support; and
manipulating the camera tube to change an orientation of the intubation stylet within the laryngeal mask.

6. The method of claim 5 wherein the step of the inserting the camera tube in the laryngeal mask includes bending the camera tube along its length to adjust an angle between the first and second imaginary lines.

7. The method of claim 5 wherein the step of inserting the intubation stylet in the laryngeal mask includes placing the intubation stylet in a groove of the camera tube formed in the camera tube exterior surface.

8. The method of claim 7 wherein the step of the placing the intubation stylet in the camera tube groove further comprises advancing the intubation stylet from the camera tube groove onto the intubation stylet guide support.

9. A method comprising:
accessing a camera tube wherein the camera tube comprises an elongate member having a length extending between opposite distal and proximal ends of the elongate member, the distal end has a camera, the camera tube has an exterior surface and an intubation stylet guide support surface extending radially outward from the exterior surface along a portion of the length adjacent to the distal end;
inserting the camera tube in a laryngeal mask;
inserting an intubation stylet in the laryngeal mask so that the intubation stylet abuts the camera tube and is supported by the intubation stylet guide support; and
manipulating the camera tube to change an orientation of the intubation stylet within the laryngeal mask.

10. The method of claim 9 wherein the step of the inserting the camera tube in the laryngeal mask includes bending the camera tube along its length.

11. The method of claim 9 wherein the step of inserting the intubation stylet in the laryngeal mask includes placing the intubation stylet in a groove of the camera tube formed in the camera tube exterior surface.

12. The method of claim 11 wherein the step of the placing the intubation stylet in the camera tube groove further comprises advancing the intubation stylet from the camera tube groove onto the intubation stylet guide support.

* * * * *